United States Patent [19]
Mayn

[11] Patent Number: 5,133,348
[45] Date of Patent: Jul. 28, 1992

[54] CONTOURED COOLING PACK

[76] Inventor: Alice M. Mayn, P.O. Box 54, Edwards, Colo. 81632

[21] Appl. No.: 764,946

[22] Filed: Sep. 24, 1991

Related U.S. Application Data

[63] Continuation of Ser. No. 495,042, Mar. 16, 1990, abandoned.

[51] Int. Cl.⁵ .................................................. A61F 7/00
[52] U.S. Cl. ..................................... 128/403; 128/402; 128/379; 383/901
[58] Field of Search ............... 128/399, 400, 402, 403, 128/379, 380; 62/530; 383/901; 126/204, 263

[56] References Cited

U.S. PATENT DOCUMENTS

| | | | |
|---|---|---|---|
| 1,308,427 | 7/1919 | Laborde | 128/402 |
| 1,522,295 | 1/1925 | Gee | 128/402 |
| 2,049,723 | 8/1936 | Pomeranz | 128/402 |
| 2,122,001 | 6/1958 | Carel | 128/402 |
| 4,347,848 | 9/1982 | Hubbard et al. | 128/402 |
| 4,552,149 | 11/1985 | Tatsuki | 128/402 |

FOREIGN PATENT DOCUMENTS 8115207  5/1981  Fed. Rep. of Germany ...... 128/402

Primary Examiner—Edward M. Coven
Assistant Examiner—Mark S. Graham
Attorney, Agent, or Firm—Beaton & Swanson

[57] ABSTRACT

A hot or cold pack with a main body portion and four radially extending portions attached thereto and integral therewith. The radially extending portions may have a width greater at their periphery than at the joining to the main body portion. The hot or cold pack is particularly useful for application to a curved contour such as breast, knee, ankle, shoulder or other body area to relieve post operative or post trauma pain and inflammation.

3 Claims, 2 Drawing Sheets

CONTOURED COOLING PACK

This is a continuation of copending application Ser. No. 07/495,042 filed on Mar. 16,1990, abandoned.

BACKGROUND OF THE INVENTION

Ice packs have been widely used in the medical field for the therapeutic treatment of swelling and inflammation and for the reduction of pain resulting from traumatic injuries or surgery. Cooling the traumatized area reduces the sensitivity of the nerve endings and also lessens swelling caused by cellular fluid expulsion. Cooling also constricts capillary vessels to reduce internal bleeding. Ice packs are particularly useful for causing this cooling because they can be applied locally without significant effect on the rest of the body, and they are also relatively convenient and inexpensive.

Many of the developments in ice packs have related to the means for attaching the ice pack to the body. U.S. Pat. No. 4,347,848 by Hubbard is a generally rectangular envelope having an open end and a pair of tie strings on each end which can be tied to one another or to a part of the body. The overall configuration of the rectangular envelope and the attaching tie strings lends itself to attachment to a limb of the body, but not to other portions of the body. Similarly, U.S. Pat. No. 4,585,003 by Meistrell is an elongated element with extended legs which wrap around on itself and adhere with Velcro brand hook and loop fastener or other adhesive means. Again, this is usable for application to a limb primarily. U.S. Pat. No. 4,517,972 by Finch carries the velcro idea even further; Velcro brand hook and loop fastener, magnetic or other adhesive means are adhered to the body and they, in turn, releasably attach to the ice pack. U.S. Pat. No. 4,645,498 by Kosak includes rectangularly shaped panels sealed around the periphery to form an envelope with Velcro brand hook and loop fastener or other attachment means that allow the envelope to wrap around a limb and seal on itself.

Other patents are directed toward the shape of the cold pack, as distinguished from the means for attachment to the body. U.S. Pat. No. 4,240,436 by Singleton relates to a specially contoured ice pack for application to the perineal region. U.S. Pat. No. 3,491,761 by Baker relates to a specially designed harness for application of ice to the head region. U.S. Pat. No. 3,871,381 by Roslonski relates to an inflatable compress which is designed to assume the shape of the body portion to which it is attached, and the claims of that patent mention that the compress may be a wrap-around bandage, an inflatable sleeve, an inflatable mitten or an inflatable boot.

Because many of the traumatic injuries to which ice packs are applied are in the limbs of the patient, most of the advances in ice packs have been directed toward ice packs which attach to a straight limb. Therefore, the ice packs are typically an elongated void, such as a rectangular envelope, with strings, velcro or other attachment means located on each end. In this way, the ice pack wraps around the limb and attaches to itself. Very little of the prior art is related to ice bags used on the body rather than on a straight limb.

The use of an ice pack on the body poses special problems. The problems are primarily that the external body configuration is such that ordinary ice bags do not conform well to the body contours, and the body is too large to allow normal ice bags to be wrapped completely around and attached to themselves. Both these problems are particularly acute with respect to, for example, the application of an ice bag to a female breast to relieve post operative pain and inflammation as occurs following breast surgery or to reduce the flow of milk following delivery. For these applications, a uniquely configured ice pack is required to conform to the body contour. Preferably, the unique configuration will conform to a variety of different possible body contours so that the same one can be used in a variety of applications. Also, preferably, the unique configuration would be usable on limbs, shoulders, ankles and other body areas in the manner of the ice packs described above.

SUMMARY OF THE INVENTION

The present invention is contoured to conform to a body contour, and also to conform to the contour of most limbs even if the limb is bent. The configuration is of a size and shape to allow a variety of means for attachment of the ice pack to both the body and limbs.

Further, the ice pack is of a multiple-ply to ensure water tightness, moisture absorption and a soft and comfortable exterior surface for application to the skin.

The ice pack comprises a central portion and radially extending members. One of the radially extending members has a resealable opening to receive ice, hot water or other similar thermal material. One or more of the radially extending members is wider at the end than at the portion where it joins the central portion of the ice pack, to allow complete body surface coverage without overlapping as the radially extended member is folded with respect to the main body portion.

The inner waterproof ply of the ice pack is a polyethylene or other waterproof plastic material of a suitable thickness. An intermediate ply is a nonwoven moisture absorbing material to draw and absorb any leakage from the ice pack and any sweat or bodily fluids. An exterior ply is a polyester flannel which forms a soft and comfortable layer to contact the patient's skin.

A BRIEF DESCRIPTION OF THE DRAWINGS

FIG. 1. shows a top plan view of the ice pack of the present invention.

DESCRIPTION OF THE PREFERRED EMBODIMENT

Figure 1:
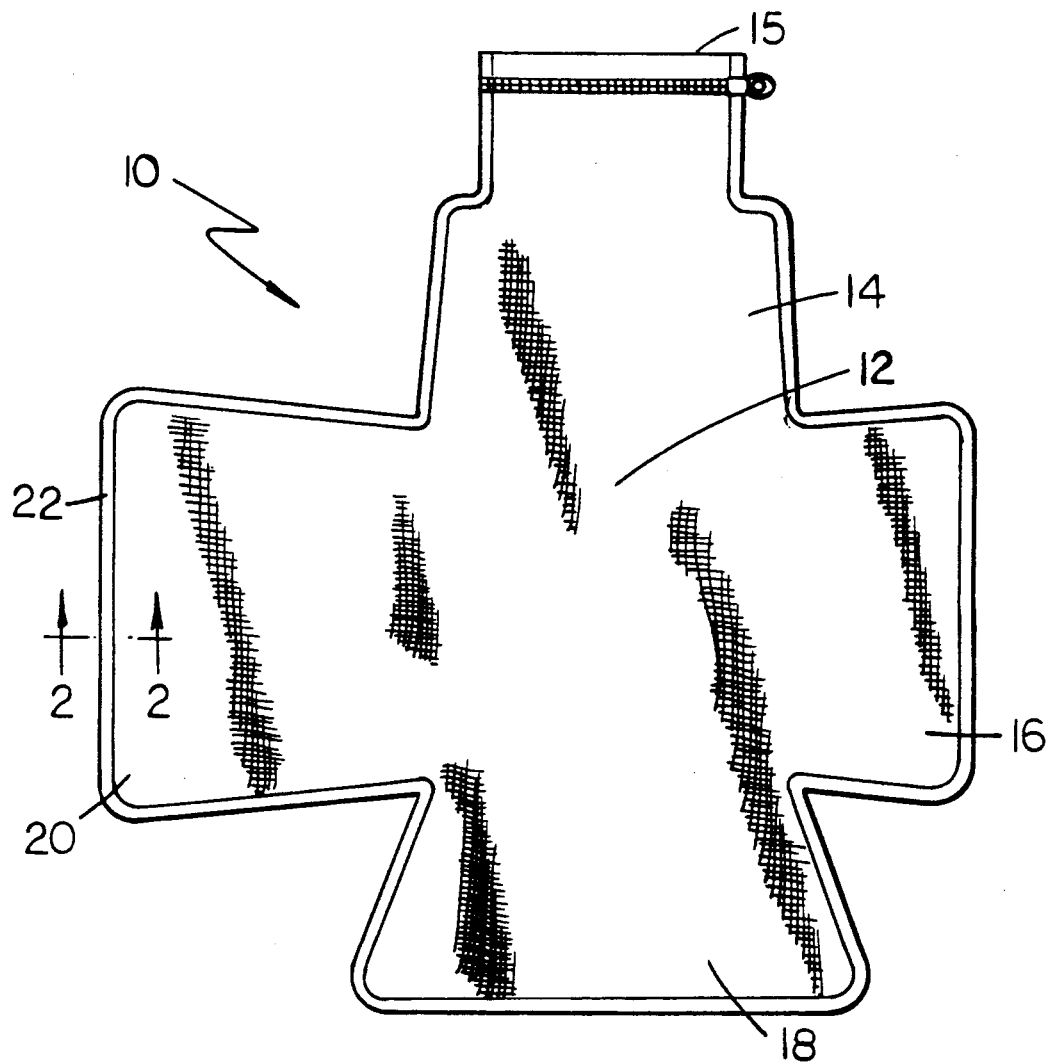

FIG. 1 shows a top plan view of the present invention 10, showing the general configuration of the preferred embodiment. The invention 10 has a central portion 12, and four radially extending portions, 14, 16, 18 and 20. The relative arrangements of the central body portion and the four radially extending portions forms a cross-shaped ice pack. One of the radially extending members has an opening 15 at the end to allow the introduction of ice, hot water or other desired thermal material. In the embodiment shown in FIG. 1, the opening 15 is in the top member——element 14——so that leakage through the opening is lessened, but the opening 15 could instead be in any of the other radially extending members, 16, 18 or 20. The opening 15 is opened and resealed with suitable closure means such as the device shown in U.S. Pat. No. 4,532,353 by Hubbard or a zipper arrangement.

Figure 2:
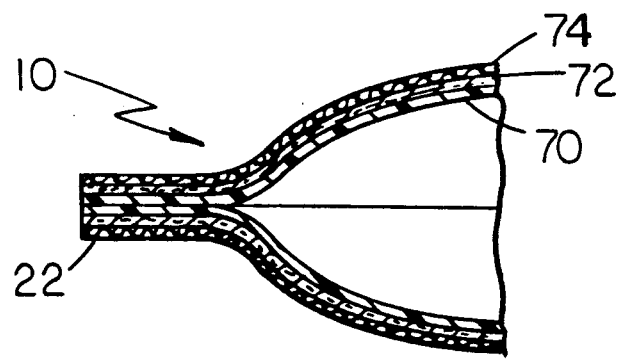
FIG. 2 shows a section view taken along lines 2—2 of FIG. 1.

The ice pack of the present invention has three plys as shown in FIG. 2. The innermost ply is a polyethylene sheet 70. It is about 2 or 3 millimeters thick to contain the liquid introduced into the ice pack through the open end. Other suitable moisture proof material for this inner sheet would be apparent to persons skilled in the art.

An intermediate layer 72 outside of the polyethylene moisture proof layer is designed to draw moisture away from both the ice pack (due to condensation on or slight leakage from the ice pack) and from the body in the form of sweat or bodily fluids. Preferably, this intermediate layer 72 has high moisture absorbing properties, yet is still thin and relatively nonthermally insulated to allow thermal transmission between the body and ice pack. The material with the brand name "Novonett" by Veratec Company has been found to be suitable for this purpose.

Finally, an exterior layer 74 surrounds the entire ice pack and contacts the skin. This exterior layer 74 should be soft and comfortable against the skin, should be relatively non-thermally insulated, and, preferably, should be a that is adhesive to whatever material that adhesive means is used to apply the ice pack to the body. In some applications this may be Velcro brand hook and loop fastener, and in those applications the exterior layer 74 should be a Velcro brand hook and loop fastener adhesive surface. It has been found that a relatively thin polyester flannel is suitable for this purpose. Of course, the exterior layer may be dyed any color desired for medical aesthetic or recognition. The two layers of each side of the ice pack are sealed together around the ice pack periphery.

The border 22 of the ice pack 10 is sealed. The seal 22 bonds the three layers of each side and bonds each side to the other side as shown in FIG. 1. This seal may be accomplished with a heat welder, ultrasonic means, an adhesive or other suitable methods.

Figure 3:
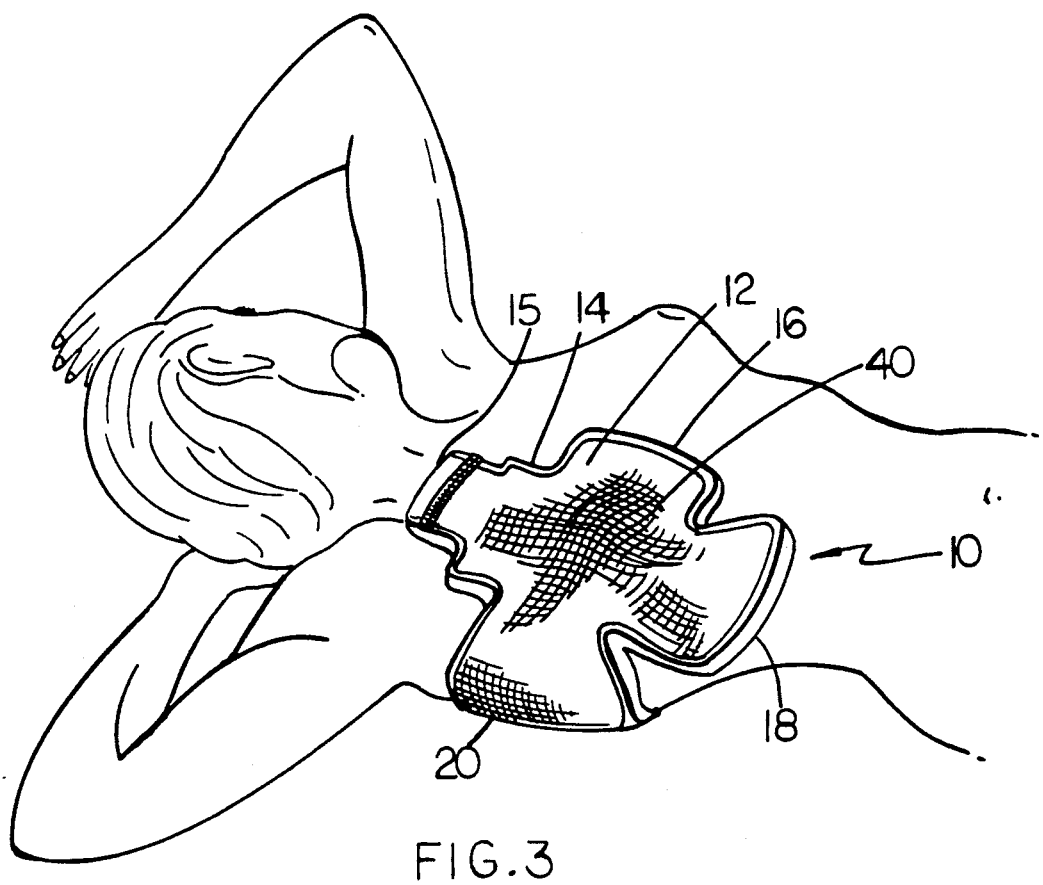
FIG. 3 shows application of the present invention to a patient's breast.

The radially extended members may be narrower at the point where they join the main body member, and wider around the periphery, as shown for members 16, 18 and 20 in FIG. 1. The widening of the radially extending members toward the periphery allows the ice pack to substantially cover all the contoured surface with a minimum of overlap and a minimum of gaping between the radially extended members as they are folded along the contours. In addition, one of the radially extending members should be longer than the radially extending member on the opposite side of the ice pack. In FIG. 1, the extra long radially extending member is radially extending member 20. As shown in FIG. 3, the purpose of this extra long radially extending member 20 is to extend under the arm on the side of the breast to which the ice pack is applied in order to reduce post operative inflammation and pain that is typical at that site following breast surgery.

FIG. 3 shows the application of the ice pack to a breast 40 to reduce post-operative pain and inflammation following breast surgery. The radially extending member 14 with the resealable open end 15 is located on the upper portion of the breast 40 above the remainder of the ice pack 10. This reduces the fluid pressure on the resealable opening 15 and consequently helps minimize leakage from that opening 15. The radially extending member 14 with the end opening 15 is then draped down the breast, along with the main body portion 12 and the opposite radially extending portion 18. The draping of those three elements—the radially extending member 14 with the end opening 15, the main body portion 12 and the opposite radially extending portion 18, form a cup shaped contour to receive the breast and allow continuous and uniform application of the ice pack. The other two radially extending members, 16 and 20, fold against either side of the breast 40. The extra long radially extending member 20 folds far enough along the side of the breast 42 to extend underneath the patient's arm 42.

Figure 4:
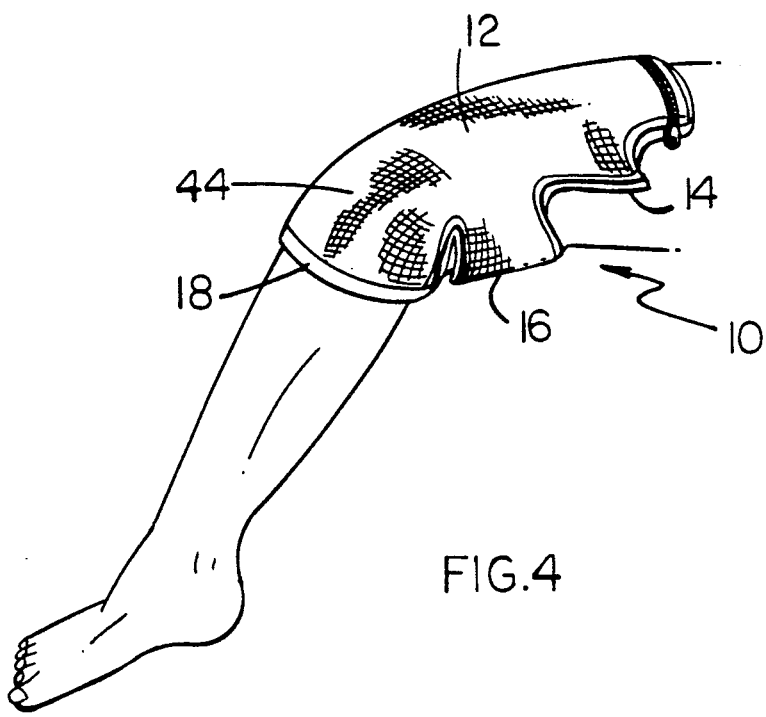
FIG. 4 shows application of the present invention to a patient's knee.

FIG. 4 shows the application of the ice pack 10 to a knee 44 to reduce post-operative pain and inflammation following knee surgery or injury. The radially extending member 14 with the end opening 15 is, again, generally located at a position higher then the rest of the ice pack 10, in order to minimize fluid pressure and possible leaking from the end opening seal 17. That radially extending member 14 is draped along the upper contour of the location to which the ice pack is applied, and the main body portion 12 and radially extending portion 18 opposite the radially extending portion 14 with the end opening 15 is draped along the bottom 46 of the knee joint conforming to the contour thereof. The two side radially extending members 18 and 20 fold along the sides of the knee 44 to substantially cover the knee joint without undue overlapping of the radially extending members or gaps there between.

What is claimed is:

1. A method for treating breast pain or inflammation of a patient comprising:

identifying the approximate location of the pain or inflammation;

placing thermal material into a hot or cold pack that includes a central portion and four radially extending portions attached to and integral with the central portion, the four radially extending portions being spaced approximately equally around the central portion, three of the radially extending portions having a tapered width with the narrow end of the taper being attached to the central portion, and two of the radially extending portions that are on opposite sides of the central portion having unequal lengths in the radial direction; and applying said hot or cold pack to the breast with the identified pain or inflammation so that the central portion is in contact with the front of the breast and the radially extending portions drape along the top, bottom and sides of the breast and so that the radially extending portion that is no longer in the radial direction than the radially extending portion that is on the opposite side of the central portion drapes along the outer side of the breast and under the arm next to the breast of the patient.

2. The method of claim 1, wherein the hot or cold pack has a soft exterior surface and a moisture-absorbing layer under the soft exterior surface, so that the application of the hot or cold pack to the patient includes absorbing excess moisture from the surface of the hot or cold pad.

3. A hot or cold pack with a center void for receiving thermal material, comprising a central portion having a thickness less than its length or width and four radially extending portions attached to and integral with said central portion and spread substantially equally around the central portion so that the central portion and four radially extending portions form a cross shape, at least one of said four radially extending portions having a tapered width, the narrow end of the tapered width being attached to and integral with the central portion and the wide end of the tapered width being at the radially extended end, and at least one of said four radially extending portions adjacent to the tapered radially extending portion having a radial length longer than the radial length of the tapered radially extending portion, and at least one of said four radially extending portions having a resealable opening for introducing and removing the thermal material.

* * * * *